United States Patent [19]

Gonser

[11] 4,200,105

[45] Apr. 29, 1980

[54] ELECTROSURGICAL SAFETY CIRCUIT

[75] Inventor: Donald I. Gonser, York, Pa.

[73] Assignee: Dentsply Research & Development Corp., Milford, Del.

[21] Appl. No.: 909,866

[22] Filed: May 26, 1978

[51] Int. Cl.$^2$ .................. A61B 17/36; A61N 3/02
[52] U.S. Cl. ................... 128/303.14; 128/303.17
[58] Field of Search .................. 128/303.13, 303.14, 128/303.17

[56] References Cited

U.S. PATENT DOCUMENTS

| | | | |
|---|---|---|---|
| 3,683,923 | 8/1972 | Anderson | 128/303.14 |
| 3,804,096 | 4/1974 | Gonser | 128/303.14 |
| 3,905,373 | 9/1975 | Gonser | 128/303.14 |
| 4,094,320 | 6/1978 | Newton et al. | 128/303.14 |
| 4,102,341 | 7/1978 | Ikuno et al. | 128/303.14 |

FOREIGN PATENT DOCUMENTS 2602517  7/1976  Fed. Rep. of Germany ...... 128/303.13

OTHER PUBLICATIONS

Gonser et al., "Design Hazards of Electrosurgical Devices", Med. Inst., vol. 10, No. 2, Mar.-Apr. 1976.

*Primary Examiner*—Lee S. Cohen
*Attorney, Agent, or Firm*—John H. Moore

[57] ABSTRACT

The invention described herein is a safety circuit for preventing burns to a patient during an electrosurgical operation. In the preferred embodiment, the safety circuit includes a pair of monitors for sensing an imbalance between current flowing to a patient from a radio-frequency generator and current returning to the radio-frequency generator from the patient. When such an imbalance occurs as a result of a stray current path to ground from the patient, an alarm is actuated. In addition, a first alternate current path between chassis ground and the radio-frequency generator and a second alternate current path between system ground and chassis ground are included. A monitor in each alternate current path is designed to actuate an alarm upon detecting a predetermined flow of current. Not only do the monitors provide back-up for each other, but the first alternate path holds near ground potential a dispersive electrode which contacts the patient. Preferably, circuitry is also included for minimizing radio-frequency leakage from the lead carrying current to the patient.

2 Claims, 1 Drawing Figure

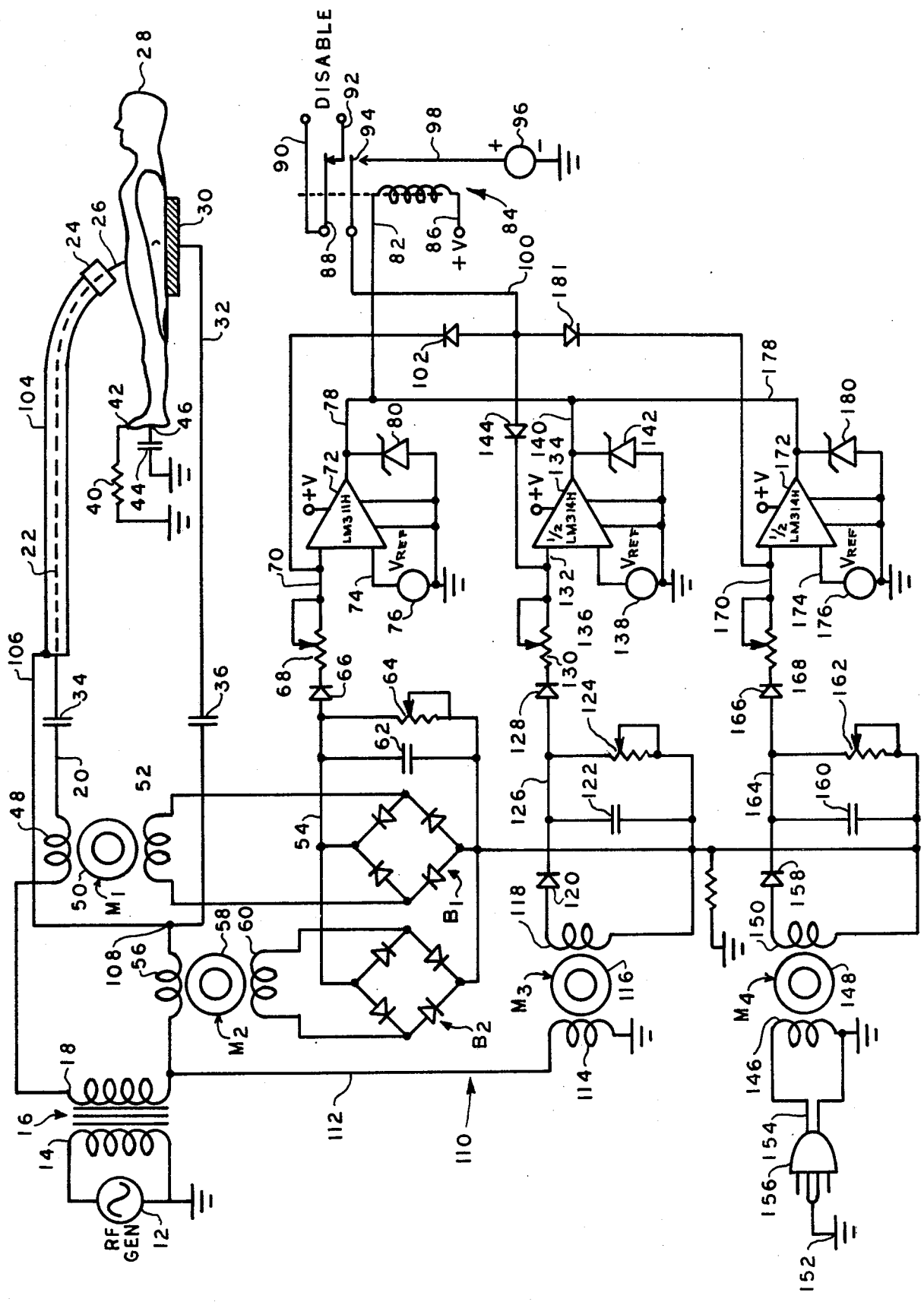

ELECTROSURGICAL SAFETY CIRCUIT

BACKGROUND OF THE INVENTION

This invention relates generally to electrosurgical devices for performing electrosurgery on a patient, and particularly to safety circuits for use therein.

In general, electrosurgical devices are used to make a surgical cut in a patient by contacting the area to be cut with an active electrode with passes RF (radio frequency) current. The RF current normally passes through the patient to a dispersive electrode on which the patient lies or to which the patient is otherwise connected, and thence back to an RF generator via a return lead. By making the dispersive electrode large in comparison to the active electrode and ensuring that the patient contacts a large area of the dispersive electrode, the RF current exiting the patient will not have a high density at any one point. Hence, the patient will not be burned by the RF current which exits his body.

While electrosurgery has enjoyed widespread success, it has been recognized that a patient may be accidentally burned by RF energy in the event that the return lead to the RF generator becomes inoperative. In that event, the RF current exiting the patient may find a stray path to ground back to the RF generator. Because the RF energy may flow to the stray path from a small area of the patient's body, the current density may be high and result in a burn to the patient.

Various suggestions have been made as to overcoming the potential burn hazards in electrosurgery. One such suggestion is to monitor the current in the active lead and the return lead, and, when an imbalance is detected between active lead current and return lead current, this is used as an indication that the RF current is finding a path back to the RF generator other than through the return lead. When that condition is detected, an alarm is sounded and/or the RF generator is disabled. U.S. Pat. No. 3,683,923 describes that proposed solution. However, that proposed solution does not take into account RF leakage from the active lead, which leakage may go undetected and present a hazard to the patient.

U.S. Pat. No. 3,905,373 offers a different solution by which leakage currents to ground are provided with an intentional alternate current path back to the RF generator. In addition, a current monitor in the alternate current path detects the presence of current flowing in the alternate path for sounding an alarm or disabling the RF generator.

An additional solution is described in U.S. application Ser. No. 543,489, filed Jan. 23, 1975, wherein the alternate current path is coupled between chassis ground and the return lead with a current monitor in the alternate current path.

Although both proposals for providing an alternate current path have been found to be effective, a failure of their respective monitors leaves the patient without protection.

Thus, even though the above-described electrosurgical safety circuits have contributed greatly to patient protection, particularly that described in application Ser. No. 543,489, a more fail safe and effective safety circuit is desirable.

OBJECTS OF THE INVENTION

Accordingly, it is an object of this invention to provide an improved electrosurgical safety circuit which overcomes the deficiencies noted above.

It is a more specific object of the invention to provide an improved electrosurgical safety circuit in which the possibility of accidentally defeating current monitors is remote, and in which a patient is continuously protected from burns resulting from RF leakage from the active lead.

DESCRIPTION OF THE FIGURE

The above-stated objects and other objects of the invention are more particularly set forth in the following detailed description and in the accompanying drawing, of which the sole FIGURE thereof depicts a circuit diagram of an electrosurgical device embodying the invention.

SUMMARY OF THE INVENTION

The objects stated above are achieved by an electrosurgical safety circuit having a plurality of current monitors disposed so that back-up is provided in the event a single monitor fails. In addition, means are included for minimizing radio-frequency leakage from the active lead carrying current to the patient.

In a preferred embodiment, a pair of monitors are included for sensing a predetermined imbalance between the current being carried to the patient from an RF generator and the current being returned to the RF generator from the patient. Should RF current find a stray path to ground from the patient, a current imbalance is detected and an alarm is actuated.

To hold the dispersive electrode near ground potential and to provide a back-up for the current imbalance monitors, a first alternate current return path is provided between chassis ground and the return lead normally returning current to the RF generator. A current monitor in this alternate path actuates an alarm when a predetermined level of current is detected. Any current passing to chassis ground via a stray path causes the current imbalance monitors to actuate an alarm. Thus, current which passes from the patient to ground not only causes the current imbalance monitors to actuate an alarm, but that same current causes the alternate path monitor to actuate an alarm. Hence, failure either of the current imbalance monitors or the alternate path monitor does not prevent an alarm from being actuated.

For further protection, a second alternate current path couples system ground to chassis ground and a monitor in this latter path actuates an alarm when the current exceeds a predetermined level. Should either the patient or the dispersive electrode be inadvertently coupled to system ground, the resulting current flowing to system ground and back to chassis ground is sensed by the latter monitor for actuating an alarm.

Should the monitor in the second alternate path fail, any current flowing from system ground to chassis ground and thence to the RF generator is sensed by the monitor in the first alternate path for sounding an alarm. Hence, both alternate path monitors serve as back-ups for each other as well as for the current imbalance monitors.

In some applications, it is contemplated that one or more of the monitors may be eliminated. For example, the current imbalance monitors may be eliminated. In that embodiment, the alternate path monitors still provide backup for each other and the first alternate path maintains the dispersive electrode near ground potential.

Irrespective of the number of current monitors provided according to the invention, it is preferred that an RF shield be disposed around the active lead to preclude patient burns from resulting from RF leakage from the active lead.

DESCRIPTION OF THE PREFERRED EMBODIMENT

Referring now to the FIGURE, there is shown an electrosurgical device 10 incorporating the preferred safety circuit. The device 10 is powered by an RF generator 12 coupled to the primary winding 14 of a transformer 16. A secondary winding 18 couples RF current via conductor 20 and an active lead 22 to a handpiece 24 terminating in an active electrode 26. By bringing the latter into contact with a patient 28, electrosurgery is performed on the patient in a conventional manner.

The RF current supplied by the active electrode 26 passes through the patient to a dispersive electrode 30 which provides a large area of contact with the patient to ensure that the current leaving the patient has a low density at each area of patient contact.

To provide a return path for the RF current, the dispersive electrode 30 is coupled via a current return lead 32 to the secondary winding 18.

As is known in the art, low frequency currents of potentially hazardous levels are generated by subharmonics, arc rectification, and modulation of the RF current. Such low frequency currents, if allowed to pass through the patient, could cause involuntary muscle stimulation. To preclude conducting such low frequency currents through the patient, the conductor 20 and the current return lead 32 include capacitors 34 and 36, respectively. The value of these capacitors is selected so as to substantially pass RF current and to substantially block the low frequency current or at least limit it to a non-hazardous level.

The capacitors 34 and 36 also limit the 50 or 60 Hertz current leakage to ground if another piece of equipment connected to the patient should fail, such as an ECG monitor. A failure of such equipment could place power line voltage on the patient, and the resulting ground-seeking currents could pass through the patient, thereby presenting a considerable hazard. Such a hazard is precluded by inclusion of the capacitors 34 and 36.

As pointed out above, it is essential to protect the patient from RF burns in the event that a stray path to ground exists from the patient. For example, if the return lead 32 should become inoperative, patient current could be returned to the RF generator via an unwanted path 40, representative of a low impedance between system ground and the patient. If the patient should come in contact with a ground object at point 42, the current density at that point will be high and the probability that a burn will occur there is also high.

Moreover, direct contact between the patient and a grounded object is not necessary to develop a burn. For example, capacitor 44 is representative of the capacitance between a point 46 on the patient and ground, such as a grounded operating table. Arc-over from the patient's body at point 46 to ground may occur, particularly if the return lead 32 is inoperative.

It is evident that any RF current which travels to the patient via conductor 20 and which returns to the RF generator via an unwanted path will not be carried by the return lead 32. Thus, an imbalance will occur between the level of current in the conductor 20 and the return lead 32.

To detect such imbalance, monitors $M_1$ and $M_2$ are included for actuating an alarm when the current imbalance exceeds a predetermined level. Thus, operating room personnel will be warned that potentially hazardous current paths to ground exist and/or that the return lead 32 is inoperative.

Referring first to the monitor $M_1$, it includes a primary transformer winding 48 serially connected with the conductor 20, a ferrite core 50, and a secondary winding 52. The output of the winding 52 is coupled to a full wave bridge rectifier circuit $B_1$. Thus, current flowing in the conductor 20 generates a voltage across the winding 52 and the rectifier circuit $B_1$ develops a corresponding DC current in the lead 54.

The monitor $M_2$ includes a primary transformer winding 56 serially connected with the return lead 32, a ferrite core 58, and a secondary winding 60. The output of the winding 60 is coupled to a full wave bridge rectifier $B_2$. Thus, current flowing in the return lead 32 develops a voltage across the winding 60, which voltage is rectified by the rectifier $B_2$ to develop a corresponding DC current in the lead 54.

As shown, the rectifiers $B_1$ and $B_2$ are oppositely poled so that the DC current developed by the rectifier $B_1$ is opposite in direction to the DC current developed by the rectifier $B_2$. Hence, if the current in the conductor 20 is equal to the current in the return lead 32 (no stray paths to ground), the net DC current in the lead 54 is zero.

Should the active lead current exceed the return lead current, there will be a net flow of DC current in the lead 54. That DC current is smoothed by a filter comprising a capacitor 62 and a variable resistor 64. The output of the filter is coupled through a diode 66 and another variable resistor 68 to an input 70 of a comparator/switch 72. The latter receives at its other input 74 a DC reference voltage from a source 76.

The output 78 of the comparator/switch 72 is coupled to a grounded zener diode 80 and to an input 82 of a relay 84. The other input 86 of the relay is coupled to a positive source of DC voltage. A normally closed contact 88 is coupled via leads 90 and 92 to a circuit for disabling the RF generator and/or sounding an alarm. Hereinafter, reference in this disclosure and claims to "sounding an alarm" is understood to alternately include the disabling of the RF generator.

The relay 84 also includes a normally open contact 94, the latter of which is coupled to a DC source 96 via lead 98.

In operation, an excess of current flowing in the active lead as compared to the return lead results in a positive DC voltage being applied to the input 70 of the comparator/switch 72. When the voltage level at the input 70 exceeds the reference voltage at input 74, a switch internal to the comparator/switch 72 grounds its output 78. Consequently, a path for current is established through the relay 84, whereupon the contact 88 is opened to sound an alarm. In addition, the contact 94 is closed to complete a circuit from the source 96, through contact 94, lead 100, and a diode 102 back to the input 70. Hence the comparator/switch 72 is caused to maintain its internal switch closed and the relay 84 remains actuated until reset in a conventional manner. The zener diode 80 protects the comparator/switch 72 from excessive transient voltages generated when the switch internal to the comparator/switch 72 closes.

To adjust the comparator/switch 72 to actuate at a given RF current imbalance, the resistors 64 and 68 may be varied to increase or decrease the level of the voltage provided from the lead 54.

The configuration and function of the monitors $M_1$ and $M_2$ is similar to that described in the aforementioned U.S. Pat. No. 3,683,923. However, the inclusion of only those monitors is not sufficient to provide a patient with the desired degree of safety, particularly with respect to RF leakage from the active lead 22. For example, should the active electrode 26 not be in contact with the patient, RF leakage will emanate from the active lead 22, the latter of which tends to act as a transmission antenna. Under those conditions, RF current will flow in the conductor 20 but very little, if any, current will flow in the return lead 32. Hence, the monitors $M_1$ and $M_2$ will sense a current imbalance and an alarm will be generated. However, the operating room personnel may consider the alarm to be a "nuisance alarm" because the patient is evidently not being burned in view of the fact that the active electrode is not contacting the patient. Notwithstanding the lack of contact between the patient and the active electrode 26, the active lead 22 may inadvertently be in contact with the patient. Under that circumstance, hazardous RF leakage from the active lead 22 may pass through the patient. Hence the alarm is not a "nuisance alarm" but is a genuine indication of a hazardous condition.

To relieve such ambiguity and to provide enhanced patient protection, the illustrated safety circuit includes an RF shield 104 surrounding the active lead 22 and a conductor 106 coupling the shield to the return lead 32 at point 108. With this arrangement, RF leakage current is returned to the RF generator and passes through the monitor $M_2$. Hence, irrespective of the level of leakage current from the active lead 22, no current imbalance is detected and no "nuisance alarm" is generated. More importantly, the patient is protected from RF leakage by the shield 104.

An additional advantage resulting from the inclusion of the shield 104 is that other operating room monitors are rendered more effective by the substantial elimination of RF interference. Without the shield 104, the excessive interference which tends to be produced may substantially interfere with the operation of those other monitors, such as ECG monitors.

Preferably, an insulator (not shown) is included between the active lead 22 and the shield 104 and over the outside of the shield 104 to provide further patient protection.

As noted earlier, it is undesirable for the dispersive electrode 30 to "float" with respect to ground. If the dispersive electrode is permitted to "float", a hazardous potential could be generated between the dispersive electrode and other adjacent equipment. Should that equipment touch the patient, a patient burn could occur at the point of contact. The use of the monitors $M_1$ and $M_2$ and/or the shield 104 does not prevent that possibility. In addition, failure of either of the monitors $M_1$ or $M_2$ will subject the patient to a potentially hazardous condition.

To overcome both aforementioned possibilities, there is included an alternate path return 110 coupled between chassis ground and the return lead 32, as shown. The return 110 includes a conductor 112 connected at one end to the return lead 32 at a point between the winding 18 and the monitor $M_2$. The other end of the conductor 112 is connected to a primary winding 114 associated with a third monitor $M_3$. A connection to chassis ground is made at the lower end of the winding 114.

The monitor $M_3$ also includes a ferrite core 116 and a secondary winding 118, the latter of which is coupled to a rectifier diode 120.

When current from the patient flows to chassis ground, that current is returned to the winding 18 via the alternate path 110. The resulting induced current in the winding 118 is half-wave rectified by the diode 120 and filtered by a capacitor 122 and adjustable resistor 124. The voltage developed at the lead 126 is coupled via a diode 128 and another adjustable resistor 130 to an input 132 of another comparator/switch 134. The other input 136 of the comparator/switch 134 receives a DC reference voltage from a source 138. The output lead 140 is coupled to a ground zener diode 142 and to the input 82 of the relay 84.

By appropriately adjusting the resistors 124 and 130, the comparator/switch 134 will actuate the relay 84 to sound an alarm whenever the current through the alternate path 110 exceeds a predetermined level. Thereafter, the comparator/switch 134 remains actuated by the signal on the lead 100 which is coupled via a diode 144 to the input 132 of the comparator/switch 134. The zener diode 142 protects the comparator/switch 134 from excessive transient voltages developed on the lead 140 in the same manner as zener diode 80.

The above-described arrangement not only provides added patient protection in the event of failure of the monitors $M_1$ or $M_2$, but also maintains the dispersive electrode 30 near ground potential by virtue of the low impedance of alternate path return 110. Of further significance is that fact that it is the same current not being sensed by the monitor $M_2$ which is being sensed by the monitor $M_3$. Hence, the same condition which results in the detection or RF current imbalance results in the monitor $M_3$ actuating the relay 84. Hence, the monitor $M_3$ will always actuate the relay 84 when, but for a malfunction of either of the monitors $M_1$ or $M_2$ (or their associated circuitry), the latter monitors would have actuated the relay 84.

Although the above-described system having monitors $M_1$, $M_2$ and $M_3$, and the shield 104 provide superior patient protection, it is possible that either the monitor $M_3$ or its associated alarm-actuating circuitry may fail to operate properly. In that event, the monitor $M_3$ would not provide a "back-up" for the monitors $M_1$ and $M_2$. To avoid such a contingency, a fourth monitor $M_4$ is included.

As shown, the monitor $M_4$ includes a primary winding 146, a ferrite core 148, and a secondary winding 150. Preferably, the winding 146 is coupled to system ground 152 via a power lead 154 and power plug 156. Thus, should the dispersive electrode 30 pass RF current to system ground, that current will be returned to chassis ground via the lead 154. From chassis ground that current flows through the alternate return path 110 back to the winding 18 associated with the RF generator 12. Hence, the monitor $M_3$ will actuate the relay 84 if the current thus returned exceeds a predetermined level.

In addition, the flow of current through the winding 146 (monitor $M_4$) induces a voltage across the winding 150. The voltage is half-wave rectified by a diode 158 and filtered by the combination of a capacitor 160 and a variable resistor 162. The resulting voltage present on the lead 164 is coupled via a diode 166 and another variable resistor 168 to an input 170 of a third comparator/switch 172. Another input 174 receives a DC reference voltage from a source 176 for comparison with the voltage present at the input 170.

When the current sensed by the monitor $M_4$ exceeds a predetermined level, the comparator/switch 172 is actuated so as to ground its output lead 178, thereby actuating the relay 84 for generating an alarm. A zener diode 180 is coupled between the output lead 178 and ground in order to protect the comparator/switch 172 from inductively induced transients. Also, a diode 181 couples the lead 100 to input 170 to hold the alarm on after it has been actuated.

The sensitivity of the circuit comprising the monitor $M_4$ and the comparator/switch 172 may be adjusted as desired by varying the resistors 162 and 168.

As a result of the inclusion of monitors $M_3$ and $M_4$ and their associated circuitry, a significant result is obtained. Specifically, the monitors $M_3$ and $M_4$ in effect operate as back-ups for each other. That is, the monitor $M_4$ actuates an alarm in response to leakage current from system ground through chassis ground and back to the RF generator even when the monitor $M_3$ or its associated alarm actuating circuitry is inoperative. On the other hand, the monitor $M_3$ acts as a "back up" not only for the monitors $M_1$ and $M_2$, but also for the monitor $M_4$ should the circuitry associated with the monitor $M_4$ fail to operate. For example, should the comparator/switch 172 fail to operate, the current flowing from system ground to chassis ground via the conductor 154 will yet be sensed by the monitor $M_3$ as that current flows upwardly through the alternate path 110. Hence, an alarm will be generated by the operation of the monitor $M_3$. Of course, monitor $M_3$ will also actuate the relay 84 whenever the patient comes in contact with chassis ground and either of the monitors $M_1$ or $M_2$ fail to operate. In addition, should the monitors $M_1$, $M_2$ and $M_3$ all fail to operate (an unlikely condition) and should the dispersive electrode or the patient be coupled to system ground, the monitor $M_4$ will yet actuate the relay 84. Hence, the novel combination of monitors provides a very high degree of safety for a patient undergoing electrosurgical treatment. Moreover, the possibility of a patient receiving a burn as a result of RF leakage from the active lead 22 is substantially eliminated by the inclusion of the shield 104.

Although the preferred embodiment of the invention includes all the monitors $M_1$ through $M_4$ and their associated alarm-generating circuitry, it will be appreciated that one or more of those monitors may be eliminated. For example, it is contemplated that the monitors $M_1$ and $M_2$ and their associated alarm-generating equipment may be eliminated. The resulting embodiment, having monitors $M_3$ and $M_4$ and their associated alarm-generating circuitry, still provides back-up in the event of failure of one of the monitors. In addition, the alternate path associated with the monitor $M_3$ holds the dispersive electrode near ground potential.

Alternately, either one of the monitors $M_3$ and $M_4$ may be eliminated. In that event, it is preferred that the alternate path 110 or its equivalent be retained to hold the dispersive electrode near ground potential. If the monitor $M_4$ is eliminated, it is preferred that a path between system ground and chassis ground be included so that any current therebetween will be sensed by the monitor $M_3$. Whatever the combination of monitors, it is preferred that the shield 104 be included.

Although the electrosurgical safety circuit embodying the invention has been described in terms of a preferred structure, it will be obvious to those skilled in the art in light of this disclosure that many alterations and modifications may be made without departing from the spirit and scope of the invention. For example, the monitors $M_1$ and $M_2$ may be arranged to actuate a first relay, the monitor $M_3$ may be arranged to operate a second relay, and the monitor $M_4$ may actuate a third relay. By using separate relays for each of the monitoring circuits, the patient is protected from failure of a single relay. All such modifications and alterations to the illustrated safety circuit are intended to be within the spirit and scope of the invention as defined by the appended claims.

What is claimed is:

1. In an electrosurgical device used in an environment having a system ground and having a radio-frequency generator coupled to chassis ground, an active electrode for performing electrosurgery on a patient, an active lead connecting the radio-frequency generator to the active electrode for carrying current from the radio-frequency generator to the active electrode, a dispersive electrode for receiving current which passes from the active lead and through the patient, and a return lead connecting the dispersive electrode to the radio-frequency generator for carrying current from the dispersive electrode back to the radio-frequency generator, an electrosurgical safety circuit, comprising:

a first monitor means for sensing the flow of current in the active lead;

a second monitor means for sensing the flow of current in the return lead;

means responsive to said first monitor means sensing a predetermined greater level of current than said second monitor means for actuating an alarm;

a first low impedance alternate current path coupled between chassis ground and the return lead so as to hold the dispersive electrode near ground potential and to provide a current path from chassis ground to the radio-frequency generator;

a third monitor means for sensing a predetermined current flow in said first alternate current path and for actuating an alarm;

a second alternate current path coupled between system ground and chassis ground so as to establish a return path from system ground to the radio-frequency generator via the first and second alternate current paths; and a fourth monitor means for sensing a predetermined current flow in said second alternate current path and for actuating an alarm, whereby radio-frequency current flowing from the patient to a ground results in an alarm generated by said first and second monitor means by virtue of a greater level of current flowing in the active lead than in the return lead irrespective of the operability of said third or fourth monitor means, said first alternate path holds the dispersive electrode near ground potential to prevent the dispersive electrode from floating to a hazardous potential, said third monitor means causes an alarm to be actuated irrespective of the operability of said first, second or fourth monitor means when current flows between chassis ground and the return lead, and said fourth monitor means causes an alarm to be activated irrespective of the operability of said first, second or third monitor means when current flows to system ground.

2. A safety circuit as set forth in claim 1 further including a radio frequency shield around the active lead and a conductor coupling said shield to the return lead, whereby a patient is protected from radio-frequency leakage current from the active lead when the active lead contacts a patient, irrespective of the operability of any or all of said monitor means.

* * * * *